(12) United States Patent
Steinhardt et al.

(10) Patent No.: US 9,885,806 B2
(45) Date of Patent: Feb. 6, 2018

(54) NARROW-BAND FREQUENCY FILTERS AND SPLITTERS, PHOTONIC SENSORS, AND CAVITIES HAVING PRE-SELECTED CAVITY MODES

(71) Applicant: THE TRUSTEES OF PRINCETON UNIVERSITY, Princeton, NJ (US)

(72) Inventors: Paul J Steinhardt, Princeton, NJ (US); Marian Florescu, Surrey (GB); Salvatore Torquato, Princeton, NJ (US)

(73) Assignee: The Trustees of Princeton University, Princeton, NJ (US)

(*) Notice: Subject to any disclaimer, the term of this patent is extended or adjusted under 35 U.S.C. 154(b) by 0 days.

(21) Appl. No.: 15/222,332

(22) Filed: Jul. 28, 2016

(65) Prior Publication Data

US 2016/0377808 A1    Dec. 29, 2016

Related U.S. Application Data

(62) Division of application No. 14/350,713, filed as application No. PCT/US2012/055791 on Sep. 17, 2012, now Pat. No. 9,465,141.

(60) Provisional application No. 61/547,480, filed on Oct. 14, 2011.

(51) Int. Cl.
| | |
|---|---|
| *G02B 6/122* | (2006.01) |
| *G01L 1/24* | (2006.01) |
| *G01K 17/00* | (2006.01) |
| *G02B 1/00* | (2006.01) |
| *B82Y 20/00* | (2011.01) |
| *G01N 21/17* | (2006.01) |
| *H01L 33/00* | (2010.01) |
| *H01L 33/16* | (2010.01) |
| *G02B 6/125* | (2006.01) |
| *G02B 5/30* | (2006.01) |
| *G02B 27/00* | (2006.01) |

(52) U.S. Cl.
CPC .............. *G02B 1/005* (2013.01); *B82Y 20/00* (2013.01); *G01K 17/00* (2013.01); *G01L 1/24* (2013.01); *G01N 21/17* (2013.01); *G02B 5/3025* (2013.01); *G02B 6/125* (2013.01); *G02B 6/1225* (2013.01); *G02B 27/0012* (2013.01); *H01L 33/0058* (2013.01); *H01L 33/0095* (2013.01); *H01L 33/16* (2013.01); *Y10T 29/49993* (2015.01)

(58) Field of Classification Search
CPC .......... B82Y 20/00; G01K 17/00; G01L 1/24; G01N 21/17; G02B 1/005; G02B 27/0012; G02B 5/3025; G02B 6/1225; G02B 6/125; H01L 33/0058; H01L 33/0095; H01L 33/16; Y10T 29/49993
See application file for complete search history.

(56) References Cited

PUBLICATIONS

Florescu et al. (Designer disordered materials with large, complete photonic band gaps, PNAS Dec. 8, 2009 vol. 106 No. 49, 20658-20663).*

* cited by examiner

*Primary Examiner* — Ling Choi
*Assistant Examiner* — Chun-Cheng Wang
(74) *Attorney, Agent, or Firm* — Medlen & Carroll, LLP

(57) ABSTRACT

Waveguides and electromagnetic cavities fabricated in hyperuniform disordered materials with complete photonic bandgaps are provided. Devices comprising electromagnetic cavities fabricated in hyperuniform disordered materials with complete photonic bandgaps are provided. Devices comprising waveguides fabricated in hyperuniform disordered materials with complete photonic bandgaps are provided. The devices include electromagnetic splitters, filters, and sensors.

2 Claims, 18 Drawing Sheets

NARROW-BAND FREQUENCY FILTERS AND SPLITTERS, PHOTONIC SENSORS, AND CAVITIES HAVING PRE-SELECTED CAVITY MODES

CROSS-REFERENCE TO RELATED APPLICATIONS

This application is a Divisional of, and claims priority to U.S. patent application Ser. No. 14/350,713, filed on Apr. 9, 2014 and entitled "Narrow-Band Frequency Filters and Splitters, Photonic Sensors, and Cavities Having Pre-Selected Cavity Modes," which is a national entry of PCT/US2012/055791, filed Sep. 17, 2012, which claims priority to U.S. Provisional Application Ser. No. 61/547,480, filed on Oct. 14, 2011, the contents of which are incorporated herein in their entirety.

This invention was made with government support under Grant #ECCS-1041083 awarded by the National Science Foundation. The government has certain rights in this invention.

FIELD OF INVENTION

The disclosure relates to hyperuniform disordered materials with complete photonic band gaps adapted to support elements of integrated electromagnetic circuits including, without limitation, electromagnetic cavities and waveguides having novel architectures.

BACKGROUND

Familiar elements of photonic and phononic systems such as waveguides, splitters, resonant cavities, and frequency filters are realized in materials in which photonic or phononic bandgaps exist or can be fabricated. Waveguides in photonic crystalline arrays (photonic crystals) have been proposed for many photonic applications, but photonic crystals have the disadvantage that they are highly anisotropic, placing tight constraints on the bending angles for waveguides and prohibiting any waveguide sections that do not align with the high symmetry directions in the crystal. Cavities in photonic crystals have also been proposed and fabricated for use in many photonic applications but, again, confinement of the radiation is anisotropic, making the properties of the cavities more difficult to control and introducing losses (leakage of the radiation). The photonic environment offered by crystalline material provides the strongest confinement along the high-symmetry directions of the crystal (along which are placed scattering centers), but is less effective along the other directions.

Phononic crystals are analogous to photonic crystals in that they are fashioned from inhomogeneous materials characterized by periodic variations in their mechanical properties (Sigalas, M., and Economou, E. J. Sound Vib, 158: 377-382, 1992). The electrical and magnetic waves that traverse photonic crystals (except in photonic bandgaps) are analogous, in some ways (Estrada, H. et al., Phys. Rev. Lett. 102: 144301, 2009) to the acoustic and elastic waves that traverse phononic materials (except in phononic bandgaps)

SUMMARY

In one embodiment, the invention provides a designed cavity fabricated in a hyperuniform disordered photonic material having a complete photonic bandgap (i.e., neither electrical or magnetic waves propagate), wherein the cavity confines a photon.

In another embodiment, the invention provides a designed cavity fabricated in a hyperuniform disordered phononic material having a complete phononic bandgap (i.e., neither acoustic nor elastic waves propagate), wherein the cavity confines a phonon.

In another embodiment, the invention provides a designed waveguide fabricated in a hyperuniform disordered photonic material having a complete photonic bandgap, wherein the waveguide confines the propagation of a photon.

In another embodiment, the invention provides a designed waveguide fabricated in a hyperuniform disordered phononic material having a complete phononic bandgap, wherein the waveguide confines the propagation of a phonon.

In other embodiments, the invention provides a device, either photonic or phononic, comprising a cavity (which may be photonic or phononic) and a waveguide (which may be photonic or phononic) fabricated in a hyperuniform disordered material (photonically or phononically responsive, as appropriate) having a complete bandgap.

In some embodiments, the aforementioned device comprises a plurality of waveguides disposed at arbitrary angles with respect to one another and in electromagnetic or phononic communication, as appropriate. In one embodiment, the communication takes place at a junction of the waveguides. In one embodiment, the junction comprises a cavity (electromagnetic or phononic) that communicates with the waveguides and can have one or more localized cavity modes with pre-selectable symmetries. In some embodiments, a spectrum of electromagnetic (or acousto-elastic) waves enters through one arm and is divided at the junction into different frequency bands, each of which is directed into different arms. In some embodiments, at least a first and a second of the aforementioned waveguides comprise line defects that differ from one another in a way that causes the first and second waveguides to transmit different frequency ranges.

In some embodiments, the device (or an element within a device) senses the presence or amount of a substance, which substance may be spaced apart from the device or associated with the device. The substance is exposed to an electromagnetic radiation such that the exposure induces a detectable mode of radiation in the device, wherein said mode is selected from a cavity mode and a waveguide mode, and wherein said mode correlates to a presence or amount of said substance in a space. In other embodiments, the device senses a force applied to a target (which may be spaced apart from the device or associated with the device) exposed to an electromagnetic radiation such that said device induces a detectable mode of said radiation in said device, wherein said mode is selected from a cavity mode and a waveguide mode and wherein said mode correlates to a presence or amount of said force at a specified location. In another embodiment, the device senses a quantity of heat applied to a target (which may be spaced apart from the device or associated with the device) exposed to an electromagnetic radiation such that said device induces a detectable mode of said radiation in said device, wherein said mode is selected from a cavity mode and a waveguide mode and wherein said mode correlates to a presence or amount of said heat at a specified location or in a specified space.

In one embodiment, the invention provides a method of detecting a presence or an amount of a substance in a specified location or space by exposing said substance to an electromagnetic radiation to induce a detectable mode of radiation in a device according to other embodiments of the invention, and correlating said induced mode to said presence or amount.

In one embodiment, the invention provides a method of detecting a presence or an amount of a force applied to a target in a specified location by exposing said target to an electromagnetic radiation to induce a detectable mode of radiation in a device according to other embodiments of the invention, and correlating said induced mode to said presence or amount of force applied.

In one embodiment, the invention provides a method of detecting a presence or an amount of a quantity of heat applied to a target in a specified location or space by exposing said target to an electromagnetic radiation to induce a detectable mode of radiation in a device according to other embodiments of the invention, and correlating said induced mode to said presence or amount of said heat.

In the aforementioned methods, the detected mode is detected as a change selected from the group consisting of phase, frequency, polarization, intensity and dielectric susceptibility, wherein said change is determined qualitatively or quantitatively.

A target may "associate" with a material, which may be a photonic or phononic material or otherwise, by binding to the material (e.g., electrostatically, by means of Van der Waal's forces, etc.), by being suspended or dispersed in the material, by covalently combining with the material, etc. "Association" herein requires only that the material, by associating with the target, undergoes a change in one or more of its properties, which change is detectable with an electromagnetic or acousto-elastic sensor and is relatable to the presence or amount of the target.

GENERAL DESCRIPTION

Photonic band gap (PBG) materials are a class of artificially created dielectric materials that carry the concept of manipulating and controlling the flow of light as well as other electromagnetic frequencies. PBG materials typically consist of a dielectric microstructure with two interpenetrating dielectric components, in which the index of refraction varies on a length scale associated with the wavelength of the radiation to be controlled. Under the right conditions, these dielectric microstructures allow the formation of a photonic band gap, a range of frequencies for which electromagnetic wave propagation is prohibited for all directions and polarizations. Then, by reducing or enhancing the effective dielectric at a certain point, it is possible to create a localized state of the electromagnetic field. This can be realized, for instance, in a two-dimensional photonic crystal consisting of dielectric cylinders in air, by removing one of the cylinders or enlarging it or changing its dielectric constant. Due to the presence of the point-like defect, a localized cavity mode is created within the photonic band gap at a certain frequency. For the cavity mode, light and electromagnetic waves in general cannot propagate anywhere outside the cavity since the trapped frequencies are in the band gap of the exterior material. Therefore, by creating the point defect, light (or any other electromagnetic wave) is localized on the length scale of the cavity, approximately the wavelength of the light or other electromagnetic wave. Such cavities have low mode volumes and as such exhibit very high quality factors (a measure of the confinement of the radiation).

Generally, photonic band gaps and the associated cavity localization and waveguide mechanisms are thought to be an exclusive property of periodic systems, namely photonic crystals. In this work, we show, in embodiments of the invention, that there exists a far wider class of cavity architectures that are built around hyperuniform disordered point patterns. Hyperuniform point patterns include periodic, quasiperiodic and certain disordered systems and are characterized by random fluctuations in the distribution of components that grow in variance not as surface area but more slowly than the surface area of the domain considered in 2d and more slowly than the volume of the domain considered in 3d. The cavities and waveguides in hyperuniform photonic structures can be computer-designed and manufactured using standard fabrication techniques used for photonic crystals and have the ability of confining and guiding both TM and TE polarized electromagnetic radiation, a property once thought to be unique to periodic structures.

Cavities in hyperuniform disordered heterostructures described herein can be introduced anywhere within the structure and with any isotropic surrounding material and can allow confinement of the electromagnetic radiation in an isotropic way in patterns that can be monopolar, dipolar, quadrupolar or high symmetry within the cavity, as desired, while at the same time the leakage of the localized radiation outside the cavity is minimized in all directions.

An embodiment includes a set of devices: new types of waveguides realized in hyperuniform disordered materials with complete photonic band gaps.

Waveguide architectures disclosed herein offer advantages over the widely employed waveguides in photonic crystals for certain applications, due to their ability to guide the light and electromagnetic waves of all polarizations through arbitrarily oriented waveguide pathways (channels) in the material and guide both polarizations of the radiation through the same waveguide channel. This is because in the case of photonic crystals or quasicrystals, the waveguiding phenomena strongly depend on the orientation of the waveguide channels with respect to the high symmetry directions of the crystal. For hyperuniform disordered structures, there are no such preferential directions—all directions are equally preferred—so the confinement around the bending region is considerably more isotropic.

An embodiment includes use of waveguides realized in hyperuniform disordered materials with complete photonic bandgaps for photonic applications where it is important to control the path of a propagating photon or electromagnetic wave and to manipulate its energy, momentum and/or polarization (collectively, its "mode"), including optical and other electromagnetic micro-circuits, especially in cases where it is advantageous to have paths with irregular shapes (not straight). An embodiment relates to novel types of photon sources that benefit from the modification of the photonic density of states due to the presence of a waveguide, such as single-photon sources.

The photonic environment offered by quasicrystalline heterostructures are more isotropic, and as such may allow loss-loss bending for wider range of angles, but they still do not allow lossless bending for arbitrary angles and may be difficult to construct. The waveguides in hyperuniform disordered heterostructures presented here allow low-loss bending for arbitrary angles. In addition, the waveguides are easier to construct and manipulate.

The waveguides disclosed herein are realized by modifying the dielectric constant along arbitrary chosen paths in a hyperuniform disordered material. The material is a heterostructure consisting of two or more materials with different dielectric constants. They are examples of designer materials in which the arrangement of the dielectrics is completely controlled in the fabrication process. To be hyperuniform, the design is chosen so that the random fluctuations in the distribution of dielectric materials of any type increases as less than the area (in 2d) or the circumference times ($\frac{2}{3}\pi r^2$) (in 3d). Waveguides in hyperuniform disordered arrangements can be incorporated in the computer design and then the material can be manufactured using the same standard techniques used for photonic crystals.

Prototype waveguide channels in hyperuniform disordered materials have been fabricated by constructing the proposed architectures consisting of dielectric cylinders and walls made out of alumina on a millimeter-centimeter scale (A1203, with a dielectric constant of 9.61). The experimental measurements of transmission in the microwave regime are in good agreement with the theoretical predictions.

An embodiment includes use of waveguides realized in hyperuniform disordered materials with complete photonic bandgaps in most cases where waveguides are used with the advantage that they can bend along arbitrarily oriented pathways. Both TM and TE polarization of light or other electromagnetic waves can be guided along the same waveguide channel.

Embodiments include a set of devices: new types of photonic cavities realized in hyperuniform disordered materials with complete photonic band gaps. An embodiment includes employing the devices in photonic applications where it is important to manipulate photons through spatial confinement and the modification of the photonic density of states due to the presence of a point-like defect (cavity). Applications may include but are not limited to micro-lasers, devices employing enhanced optical and other electromagnetic nonlinearities and single-photon sources. An embodiment relates to novel types of light sources that benefit from the modification of the photonic density of states due to the presence of a linear defect (waveguide), such as single-photon sources.

The new cavity architectures herein may offer advantages over the widely employed cavities in photonic crystals for certain applications, due to their ability to confine the light in a statistically isotropic photonic environment. Also, unique to these cavities is the simultaneous localization of both polarizations of the radiation, TM and TE, in the same physical structure. In the case of photonic crystals or quasicrystals, the localization phenomena strongly depend on the position of the cavity within the unit cell: the best confinement is realized along the high symmetry directions of the crystal, while in other directions the crystal is less effective in confining the radiation. For hyperuniform disordered structures, there are no such preferential directions and the confinement is considerably more isotropic. Calculations demonstrate that by precisely tuning the physical properties of a cavity in hyperuniform disordered structure, it is possible to accurately control the localized photonic mode pattern within the cavity and induce a rich variety of spatial symmetries in the spatial distribution of the electromagnetic mode.

The cavities can be realized by modifying the dielectric constant around an arbitrary point in a hyperuniform disordered material. The material is a heterostructure consisting of two or more materials with different dielectric constants.

They are examples of designer materials in which the arrangement of the dielectrics is completely controlled in the fabrication process. To be hyperuniform, the design is chosen so that the random fluctuations in the distribution of dielectric materials of any type increases as less than the area (in 2d) or the circumference times ($\frac{2}{3}\pi r^2$) (in 3d). The dielectric materials act as scattering centers for electromagnetic radiation. The cavity can be implemented by including in the design the reduction in the size or complete elimination of the scattering center at that center of the cavity, or by gradually filling one of the scattering cells of the heterostructure with a high-index of refraction material. Due to the presence of this intentional defect, a localized mode is created within the band gap of the photonic heterostructure and the electromagnetic radiation can be spatially localized by exciting this defect mode. The underlying hyperuniform disordered heterostructure in which the defect is introduced must be constructed in a manner that is hyperuniform; that is, the random fluctuations in the distribution of components must grow as less than the area (in 2d) or the circumference times $\frac{2}{3}\pi r^2$ (in 3d).

Full computer simulations of cavities in two-dimensional structures and three-dimensional structures with axial symmetry have demonstrated their ability to localize the electromagnetic radiation using the same computer algorithms that accurately predict the photonic cavity properties for photonic crystals and quasicrystals. Prototypes for the hyperuniform disordered materials without defects and with waveguide defects have been constructed and experimental results with the same agree with the computer simulations. Since simulations and experiments agree well in these two cases, and there is no new physics involved with the cavities, simulations and experiments should work well with cavities as well.

An embodiment includes use of cavities realized in hyperuniform disordered materials with complete photonic bandgaps in most cases where cavities are used, with the advantage that they can confine the radiation in a more isotropic way and can realize confined modes exhibiting a variety of symmetries. Both TM (transversal magnetic) and TE (transversal electric) polarization of light can be confined isotropically in the same physical structure.

Hyperuniform disordered solids herein may have an advantage in that they are less sensitive fabrication defects since they are disordered to begin with. This advantage may mean that fabricating waveguides and cavities as described herein is easier.

BRIEF DESCRIPTION OF THE DRAWINGS

The patent or application file contains at least one drawing executed in color. Copies of this patent or patent application publication with color drawings will be provided by the Office upon request and payment of the necessary fee.

The following detailed description of the preferred embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings: The drawings filed herewith include illustrations of photonic cavities and waveguides and are incorporated herein as if fully set forth.

DEFINITIONS

Figure 1:
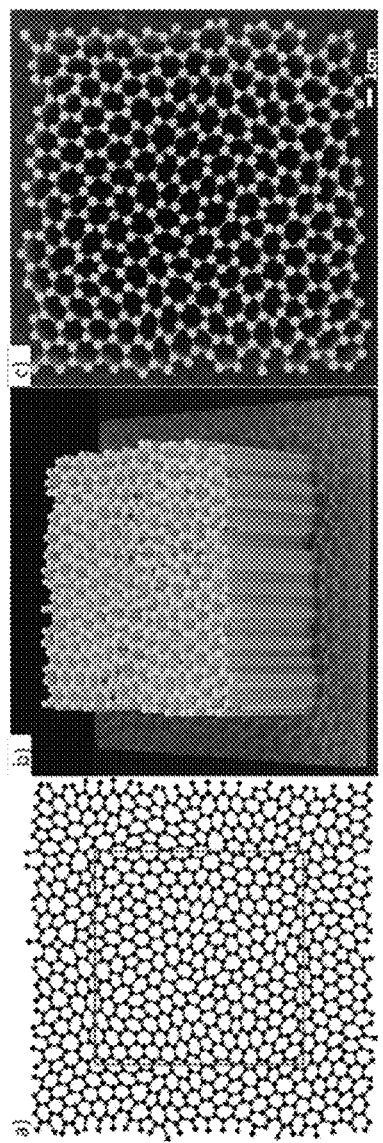
FIG. 1 shows the design of a hyperuniform disordered structure and photographs in side view and top view.

To facilitate an understanding of the various embodiments of this invention, a number of terms (which may be set off in quotation marks in this Definitions section) are defined below. Terms used herein (unless otherwise specified) have meanings as commonly understood by a person of ordinary skill in the areas relevant to the present invention. As used in this specification and its appended claims, terms such as "a", "an" and "the" are not intended to refer to only a singular entity, but include the general class of which a specific example may be used for illustration, unless the context dictates otherwise. For example, the phrase "chosen from A, B, and C" and the like, as used herein, means selecting one or more of A, B, C. The phrase "at least one" followed by a list of two or more items, such as "A, B, or C," means any individual one of A, B or C as well as any combination thereof. Certain terminology is used in the following description for convenience only and is not limiting.

As used herein, absent an express indication to the contrary, the term "or" when used in the expression "A or B," where A and B refer to a composition, product, etc., means one or the other, or both. As used herein, the term "comprising" when placed before the recitation of steps in a method means that the method encompasses one or more steps that are additional to those expressly recited, and that the additional one or more steps may be performed before, between, and/or after the recited steps. For example, a method comprising steps a, b, and c encompasses a method of steps a, b, x, and c, a method of steps a, b, c, and x, as well as a method of steps x, a, b, and c. Furthermore, the term "comprising" when placed before the recitation of steps in a method does not (although it may) require sequential performance of the listed steps, unless the context clearly dictates otherwise. For example, a method comprising steps a, b, and c encompasses, for example, a method of performing steps in the order of a, c, and b; c, b, and a, and c, a, and b, etc.

Unless otherwise indicated, all numbers expressing quantities of ingredients, properties such as molecular weights, reaction conditions, etc., as used in the specification and claims, are to be understood as being modified in all instances by the term "about." Accordingly, unless indicated to the contrary, the numerical parameters in the specification and claims are approximations that may vary depending upon the desired properties sought to be obtained by the present invention. At the very least, and without limiting the application of the doctrine of equivalents to the scope of the claims, each numerical parameter should be construed in light of the number of reported significant digits and by applying ordinary rounding techniques. Notwithstanding that the numerical ranges and parameters describing the broad scope of the invention are approximations, the numerical values in the specific examples are reported as precisely as possible. Any numerical value, however, inherently contains standard deviations that necessarily result from the errors found in the numerical value's testing measurements.

The term "not," when preceding and made in reference to any particular named composition or phenomenon, means that only the particularly named composition or phenomenon is excluded.

The term "altering" and grammatical equivalents as used herein in reference to the level of any substance and/or phenomenon refers to an increase and/or decrease in the quantity of the substance and/or phenomenon, regardless of whether the quantity is determined objectively, and/or subjectively.

The terms "increase," "elevate," "raise," and grammatical equivalents when used in reference to the level of a substance and/or phenomenon in a first instance relative to a second instance, mean that the quantity of the substance and/or phenomenon in the first instance is higher than in the second instance by any amount that is statistically significant using any art-accepted statistical method of analysis. Correspondingly, the terms "reduce," "inhibit," "diminish," "suppress," "decrease," and grammatical equivalents when used in reference to the level of a substance and/or phenomenon in a first instance relative to a second instance, mean that the quantity of substance and/or phenomenon in the first instance is lower than in the second instance by any amount that is statistically significant using any art-accepted statistical method of analysis.

The terms "photon" and "phonon," strictly speaking, are terms of art in quantum mechanics. Herein, however, since all embodiments of the invention are based on classical mechanical principles, the terms are used interchangeably with their counterparts in classical mechanics, viz., "electromagnetic wave" ("light" if the wave is in the visible spectrum) and "acousto-elastic wave" ("sound" if the wave is in the range of human audition), respectively.

The term "photonic material" relates to a substantially transparent material characterized by having local dielectric contrasts distributed within the material, which contrasts cause electromagnetic waves/photons entering the material to be reflected, refracted, absorbed, dispersed or otherwise affected, with the result that certain frequencies of the impinging waves/photons may not exit the material but may be retained as waves/photons within the material. It will be understood that the electromagnetic waves/photons discussed herein may be referred to as "light" or "light waves" whether or not the frequencies of the particular waves/photons being referred to are in the visible part of the spectrum.

The term "band" refers to a finite range of electromagnetic waves or acousto-elastic waves of different frequencies within the electromagnetic or acousto-elastic spectrum. When a subset thereof is absent from the band, a "band gap" (band-gap, bandgap) exists. Since photonic and phononic materials create such gaps by prohibiting passage of a range of frequencies within the band (a "sub-band"), the term "bandgap" often is used in reference to the material, not to the absent wave energy. Herein, the term may refer to either one, as the context so admits.

The term "complete bandgap" (or "absolute bandgap") in the context of electromagnetic radiation (which comprises electrical and magnetic waves in a mix of polarizations) means a band from which both types of wave are absent. In the context of acousto-elastic waves in solids, the term means a band from which acousto-elastic waves oscillating in the direction of propagation and acousto-elastic waves oscillating transverse to the direction of propagation are both absent. Equivalently, the term refers to a photonic element in a photonic material within which neither an electrical or a magnetic wave (having a particular frequency and direction) is allowed passage, or to a phononic element in a phononic material within which neither a longitudinal nor a transverse wave is allowed passage. It is understood that the bulk material outside the photonic or phononic element forbids passage of waves (at least within a band).

The term "photonic element" refers to one or more of the local dielectric contrasts in a photonic material or to a region(s) in the material from which dielectric contrast has been removed or quantitatively altered. Manipulation of photonic elements leads to configurations that variously confine ("trap" or "guide") waves/photons within the material, sometimes to practical effect. Therefore, the term "photonic element" may refer generically to such configurations. Thus, "waveguides," "resonant cavities," "photonic filters," and "photonic splitters" are photonic elements.

The term "phononic element" refers to one or more of the local contrasts in a mechanical property of a phononic material or to a region(s) in the material from which the mechanical contrast has been removed or quantitatively altered. Manipulation of phononic elements leads to configurations that variously confine ("trap" or "guide") acousto-elastic waves within the material, sometimes to practical effect. Therefore, the term "phononic element" may refer generically to such configurations. Thus, "waveguides," "resonant cavities," "phononic filters," and "phononic splitters" are phononic elements.

The term "in photonic communication" refers to a condition wherein a first photonic element can receive from or transmit to a second photonic element a photon/electromagnetic wave. Similarly, "in phononic communication" refers to a condition wherein a first phononic element can receive from or transmit to a second phononic element an acousto-elastic wave.

The term "photonic cavity" as used herein relates to a device (or an element within a device) realized in a material that prohibits propagation in at least one direction of either the electrical or the magnetic component, or both, of electromagnetic radiation (energetic particles or waves that are capable of self-propagating in a vacuum at one or more frequencies, the cavity characterized in that it can contain or "trap" within it at least one state or mode of that electromagnetic radiation. That is, the radiation can enter the cavity (and sometimes resonate therein) but cannot propagate out of the cavity. When a heterostructure assembled from two types of "building blocks," each type contrasting in refractive index, is perturbed by removing or adding a single block, a "point defect" is created. If that defect is located within a band-gap region of the assembly, it can create a cavity in which the photonic wave/particle remains confined, theoretically forever. The term "phononic cavity" is intended to convey the same concept, except that the trapped mode comprises an acousto-elastic wave.

The term "mode" relates to a state or configuration of electromagnetic or acousto-elastic waves, the state characterized by an energy, a momentum and a polarization.

Localized modes, wherein propagation is not allowed, may exhibit various "mode symmetries" (e.g., monopole, dipole, quadrupole, etc.) depending upon the number and shape of the fields generated by the "back and forth" travel from one edge of a cavity to another of the trapped wave(s).

The term "electromagnetic waveguide" as used herein relates to a device (or an element within a device) realized as a channel in a material that prohibits propagation of one or more polarizations (electromagnetic radiation comprises an integrated electrical and a magnetic component separated as polar opposites) at one or more frequencies, the waveguide characterized in that it can contain and allow the propagation therein of at least one state or mode of that electromagnetic radiation (otherwise prohibited in the material), not unlike an electromagnetic cavity. Waveguides, however, allow certain modes to travel through and out of the guide path. Waveguides are created by designing and arranging a "line" of point defects in a bandgap region of a heterostructure. Similarly, phononic waveguides contain and allow the propagation therein of at least one state or mode of acousto-elastic radiation.

The term "electromagnetic polarization" relates to the fact that electromagnetic radiation is a combination of a time-varying electrical and magnetic impulse, each oscillating in a plane of its own. The planes are disposed orthogonally to each other, which means that the electrical wave is maximally separated from the magnetic wave, i.e., the waves are "polarized." The intersection of the planes describes the direction of the radiation. The planes are oriented transverse to the direction of radiation. Thus, the radiation is polarized into a "transverse electrical" mode and a "transverse magnetic" mode. In a waveguide, only oscillations that "fit" within the boundaries of the channel can exist. Guided radiation, therefore, will not pass through the channel at any frequency that is disallowed because its transverse electrical wave doesn't fit or because its transverse magnetic wave doesn't fit. In the context of acousto-elastic waves in solids, polarization refers to the fact that the waves can oscillate in the direction of wave propagation or transverse to the direction of propagation.

The term "splitter" as used herein relates to a plurality of waveguides configured to meet at a junction, optionally with an associated cavity, in a bulk material that prohibits the propagation of radiation for a finite range of frequencies. The waveguides are in electromagnetic (or acousto-elastic)

communication. In preferred embodiments, the junction is designed such that a mixture of waves, prohibited in the bulk material, can enter one arm and then be divided by frequency as the designer so determines. Also as the designer so determines, the divided waves can be directed into the other arms. An arbitrary number of branches is contemplated and a branch angle may approach 0° at one extreme and 180° at the other.

The energy, momentum and/or polarization state of the radiation, may be detected as a change in phase, frequency, or intensity.

The states or modes of radiation that are allowed to pass into the other arms may be determined by the energy, momentum and polarization of the radiation to affect its phase, frequency and intensity.

The term "filter" relates to a device (or an element within a device) that selects a spectrally narrow range of frequencies out of a broad incoming range of frequencies to create a first, narrow band and a second band, different from the broad incoming band because of the extraction, by splitting, of the first band. Depending upon the application, the narrow-band may be selected for further use and the rest of the incoming frequencies reflected or absorbed (a "band-pass" filter). In a "stop-band filter" one or more narrow bands are reflected/absorbed and the rest of the incoming frequencies are transmitted for further use.

The term "electromagnetic sensor" relates, in one aspect, to a device (or an element within a device) for sensing the presence or amount of a particular target substance in a specified location or space or time. In another aspect, the term relates to a device (or an element within a device) for sensing the presence or amount of a force applied to a target. In another aspect, the term relates to a device (or an element within a device) for sensing the presence or amount of heat in a specified location or space. In some embodiments, the target substance or the applied force or heat induces (or quenches) a detectable cavity mode in the electromagnetic radiation. In some embodiments, the target induces (or quenches) in the device a detectable waveguide mode in an electromagnetic radiation. In general, the target or the applied force or the heat induces a change in the energy, momentum and/or polarization state of the radiation, which may be detected as a change in phase, frequency, or intensity of the radiation in the device. A "phononic sensor" operates similarly, except that acousto-elastic radiation is employed instead of electromagnetic radiation.

A target may "associate" with a photonic or phononic material by binding to the material (e.g., electrostatically, by means of Van der Waal's forces, etc.), by being suspended or dispersed in the material, by covalently combining with the material, etc. "Association" herein requires only that the material, by associating with the target, undergoes a change in one or more of its electromagnetic properties, which change is detectable with an electromagnetic sensor and is relatable to the presence or amount of the target.

DETAILED DESCRIPTION OF THE PREFERRED EMBODIMENTS

Until recently, photonic band gaps and the photon-confining cavities and waveguides that can be created within them were thought to require materials (photonic crystals and certain quasicrystals in particular) characterized by a periodically repeating internal structure. Band gaps occur in crystals only in severely proscribed orientations. Quasicrystals can relax this constraint of anisotropy that limits the versatility of crystals for use in photonic systems, without at the same time foreclosing on the possibility of constructing complete (i.e., "absolute") band-gaps therein. Because the photonic environment offered by quasicrystalline heterostructures is more isotropic than that of crystals, a photonic confinement cavity in a quasicrystal can trap wave energies entering the cavity from a wider variety of angles than corresponding cavities in crystals can. Similarly, waveguides in quasicrystals may be "bent" over a larger selection of bend angles than waveguides in crystals, and still transmit losslessly or with low loss. Quasicrystals do not allow lossless bending for arbitrary angles, however, even if scattering elements with very high refractive index are selected for the construction of the quasicrystal. Quasicrystals have been designed by placing light-scattering centers at points distributed quasiperiodically in two dimensions (U.S. Pat. No. 8,243,362) and in three-dimensions (U.S. Pat. No. 8,064,127). U.S. Pat. Nos. 8,243,362 and 8,064,127 are incorporated herein by reference for all purposes as if fully set forth herein.

More recently, materials that have their light-scattering centers distributed in a somewhat disordered manner in a pattern that deviates from both the periodic and the quasi-periodic have been designed (WO 2011/005530, incorporated herein by reference for all purposes as if fully set forth herein). Such materials further relax the anisotropy constraint (essentially to zero under certain specified conditions) without denying the designer the opportunity to construct complete band gaps therein. The arrangement of scattering centers in periodic and quasiperiodic systems referred to in U.S. Pat. Nos. 8,064,127, 8,243,362 and in the disordered systems disclosed in WO 2011/005530 share the statistical property of hyperuniformity (defined infra).

Non-hyperuniform disordered three-dimensional ("3D") photonic solids have been discussed (Edagawa, K. et al., Phys. Rev. Lett 100: 013901, 2008; Imagawa, S., et al., Phys. Rev. Lett 82: 115116-1, 2010), but systematic convergence tests using samples of increasing size would need to be performed to determine whether or not bandgaps can actually persist in that type of disordered environment and whether or not any of them (if any exist) could be complete, that is, capable of prohibiting the transmission of both the magnetic wave that oscillates in a first plane transverse to the direction of propagation (TM) and the electrical wave that oscillates in a second plane also transverse to the direction of propagation but disposed orthogonally to the first plane (TE).

Knowledge that one can create materials that are disordered but nevertheless exhibit complete bandgaps does not carry with it any substantive assurance that functional electromagnetic devices can be fabricated in disordered materials, hyperuniform or otherwise. Given the reflection, backscatter, leakage and other quality factor problems that such disorder would suggest to persons skilled in the art, effective waveguides, microcavities, filters, resonators, lasers, switches, modulators, etc. of any kind might seem beyond reach, not to mention waveguides that bend or join at arbitrary angles, or resonant cavities with selectable cavity mode symmetries. Discouraging to the notion that waveguides or cavities—particularly ones this versatile—could be fabricated in the face of such disorder are at least the following facts: Disorder in periodic systems "shrinks" bandgaps (Rya, H. et al., Phys. Rev. B 59: 5463, 1999) and can close them entirely (Meisels, R. et al. J. Optics A: Pure and Applied Optics 9: S396, 2007). Also, it is well documented that disorder has a deleterious effect on waveguiding (Hughes, S. et al. Phys. Rev. Lett. 94: 033903, 2005) and on the quality factor of confinement cavities (Gerace, D. and Andreani, L., Photon. Nanostruct. Fundam. Appl. 3: 120, 2005).

Applicants have experimentally demonstrated an isotropic complete photonic bandgap in a 2D disordered hyperuniform dielectric material (dielectric contrast of 8.76) that has no long-range translational order and shows no Bragg scattering. Surprisingly, given the foregoing, Applicants have shown that the artisan can, in fact, exploit the bandgap capabilities and the isotropy of the material to create novel functional waveguides of arbitrary shape, as well as cavities with selectable cavity modes in an environment of constrained disorder. Further, the freeform waveguides can channel photons robustly in arbitrary directions with facile control of transmission bandwidth and sharp filtering. Finally, the waveguides can be decorated to produce sharp resonant structures. Accordingly, embodiments comprising such elements, including new devices and uses thereof, are described and claimed herein.

Hyperumform Disorder.

The concept of hyperuniformity was first introduced as an order metric for ranking point patterns according to their local density fluctuations at large length scales (Torquato, S. and Stillinger, F., Phys. Rev. E 68: 04113, 2003). A point pattern in real space is hyperuniform if the number variance $a(R)^2$ within a spherical sampling window of radius R (in d dimensions), grows more slowly than the window volume for large R, i.e., more slowly than $R^d$. In the context of the disordered networks of dielectric cylinders and walls that comprise embodiments of the invention, examples of which embodiments are the experimental samples investigated herein, each cylinder is connected to three neighbors (trivalency) and the hyperuniformity condition is generated by placing the axial centers of the cylinders or rods on a point pattern in which the number variance of points in a "window" of radius R, where $\sigma(R) = \langle N_R^2 \rangle - \langle N_R \rangle^2$, is proportional to R. Crystalline and quasicrystalline point patterns trivially satisfy this property but, as noted supra, it is also possible to have isotropic, disordered hyperuniform point patterns. In Fourier space, hyperuniformity means the structure factor S(k) (a determinant of the extent to which a dielectric structure scatters light) approaches zero as $|k| \to 0$. k is the momentum of the wave. The hyperuniform patterns that are relevant here are restricted to the subclass in which random fluctuations of the pattern in the domain under consideration cause the number variance to grow like the window surface area for large R, e.g., $a^2(R) = AR$ in two-dimensions, or $a^2(R) = AR^2$ in three dimensions, up to small oscillations (Torquato, S. and Stillinger, F., Phys. Rev. E 68: 04113, 2003; Zachary, C. and Torquato, J., J. Stat. Mech.: Theory Exp. P12015, 2009). The photonic design pattern of hyperuniform disordered materials (such as the samples investigated herein) has uniform nearest neighbor connectivity, hyperuniform long-range density fluctuations similar to crystals and, at the same time, random positional order. The combination results in a circularly symmetric diffuse structure factor S(k) similar to a glass, but with the property that S(k) approaches zero as $|k| \to 0$.

By further constraining the disorder, one can produce hyperuniform "stealthy" point patterns for which the structure factor S(k) is isotropic and precisely equal to zero for a finite range of wavenumbers $0 \le k \le k_C$ for some positive critical wavevector, $k_C$. Embodiments of the invention are not limited by any theory as to how the embodiments work, but it is believed that, combined with the condition that the structure be derived from a point pattern, increasing $k_C$ results in a narrowing of the distribution of nearest-neighbor distances. The net effect is to increase the bandgap so that one obtains the largest band gaps for a given dielectric constant (Florescu et al., PNAS 106: 20658, 2009). Point patterns that conform to any chosen statistical parameter can be computer-designed by methods well-known to persons skilled in the art. Hyperuniform photonic materials may then be constructed by decorating the point pattern (in this case a hyperuniform stealthy pattern) with dielectric materials according to the protocol described in Florescu, M. et al., PNAS 106: 20658, 2009 and outlined in WO 2011/005530. Manufacturing techniques to perform the "decoration" steps are well-known in the art. The hyperuniform disordered photonic materials display an unusual combination of physical characteristics that can be exploited in various embodiments of the invention described and claimed herein. These include statistical isotropy, multiple scattering resulting in localized states, and large, robust, complete bandgaps, A wide variety of "decoration" materials are suitable. Materials will be selected by persons of skill in the art to meet fabrication constraints for the wavelength regime of interest and to comport with the nature of the energy (vibrational, electronic, photonic) whose transmission is to be controlled. Photonic crystals (periodic) having structural elements as small as the nanometer range have been fabricated (e.g., U.S. Patent Appl. No. 2008/0232755, incorporated herein by reference for all purposes as if fully set forth). Photonic devices that embody aspects of the invention preferably comprise materials of relatively high dielectric constant, but hyperuniform disordered structures tend to be less demanding in this respect than quasicrystals.

Samples for investigative use herein were fabricated with commercially purchased $Al_2O_3$ cylinders and walls cut to designed heights and widths. The dimensions of the cylinders and walls and their spacings are not critical in any absolute sense. The values can be re-scaled together to fix the frequency range of the photonic band-gap that is optimal for a given embodiment and in part on the preferred dimensions of the device in which the bandgap is being deployed. The hyperuniform point patterns on which the samples were built were generated by the collective coordinate method set forth in Torquato, S. and Stillinger, F., Phys. Rev. E 68: 04113, 2003 with stealthy order parameter $\chi=0.5$. A typical PBG size for structures with $\chi=0.5$ is $\Delta\omega/\omega C=37\%$, where $\omega C$ is the central frequency of the gap. For simplicity, PBGs for transverse magnetic (TM) polarized radiation were considered in the illustrative embodiments exemplified herein. The same analysis for transverse electric (TE) polarized radiation is well within the capability of the skilled artisan.

Data on the first physical realization of a hyperuniform stealthy design (FIG. 1) are presented herein. FIG. 1(a) shows a section of the cylinders and wall network that decorate the 2D hyperuniform disordered structure investigated. The area highlighted in the red box is the exact structure used for the study. FIG. 1(b) and FIG. 1(c) are side view and top view photograghs of the $Al_2O_3$ cylinders and walls assembled in accordance with the hyperuniform disordered design. Interactions of the structure with electromagnetic radiation are given in the Examples, infra. Other physical realizations are readily achieved simply by removing and replacing cylinders and walls in conformity with the procedures described herein.

It is to be noted that the use of $Al_2O_3$ and air is not limiting. Any materials that create a dielectric contrast and are otherwise suitable for fabricating cylinders, sheets, foils, etc. are candidates In air, alumina, silicon, silicon nitride, gallium arsenide, indium phosphide, silica, indium antimonide (for mid infra-red frequencies) and gallium phosphide could apply, among others, including metals (titanium, for example) embedded in acrylate or similar polymers.

Waveguides, Splitters and Frequency Filters.

Figure 3:
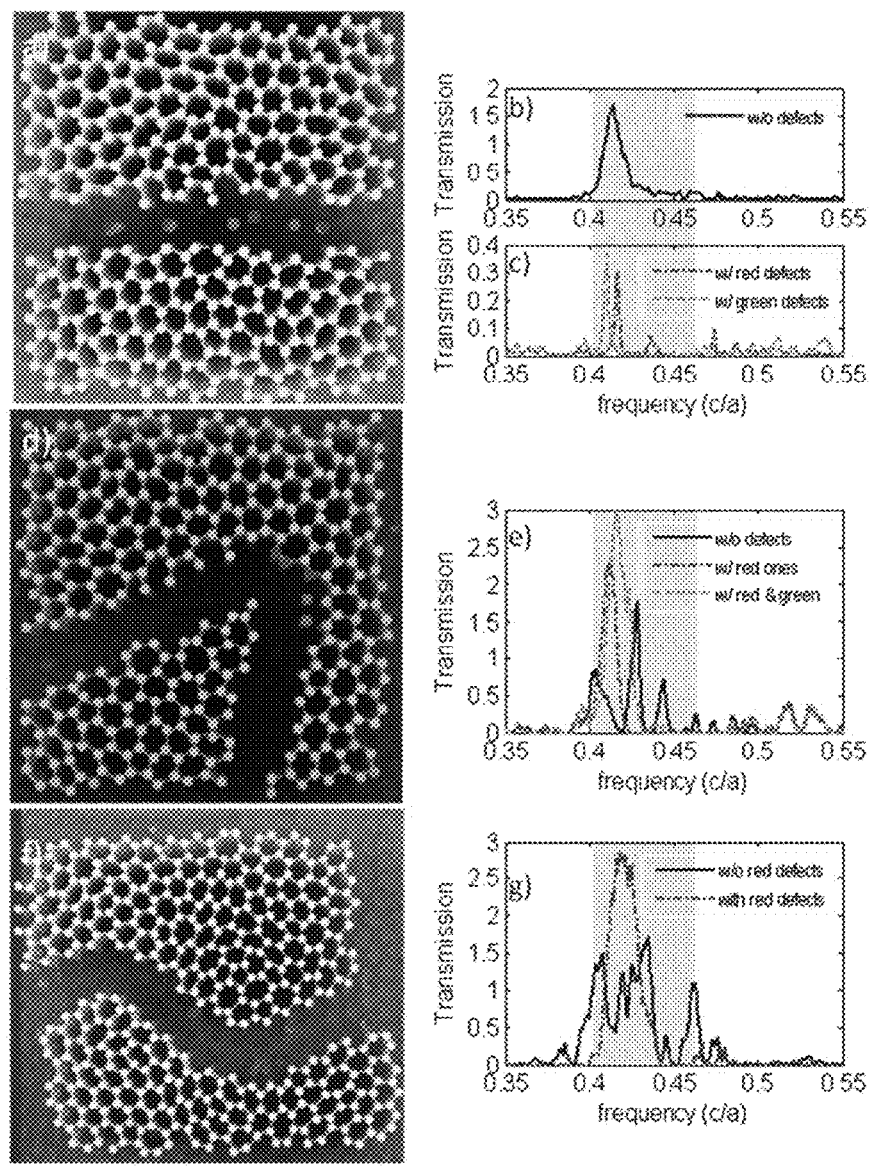
FIG. 3 shows photographs of wave-guiding channels and plots of TM-polarized transmission therethrough.

In contrast to photonic crystals, where waveguides are limited in their direction and angularity by crystal symmetries (Lin, S-Y et al., Science 282: 274, 1998), the experimental samples studied herein easily accommodate channels with arbitrary bending angles. It is also easy to decorate their sides, corners and centers with cylinders and walls for tuning and optimizing the transmission bands. FIG. 3(d) shows a waveguide with a sharp 50° bend made by removing cylinders and walls in a path ~2a wide. FIG. 3(e) shows the measured transmission. The transmission is comparable to that in the straight channel with unity transmission despite the sharp bend, and it is adjustable by modifying defects. Even more remarkable is the "S" shaped freeform waveguide shown in FIG. 3(f). As in the other channel designs, the transmitting and receiving horns are parallel to the input and output of the channel and the transmission is of order unity (FIG. 3(g). Again, transmission bands can be easily improved and flexibly tuned using defect cylinders.

The channels function in a 2D disordered hyperuniform dielectric material with an isotropic complete PBG (all angles of propagation in the plane and all polarizations). The disordered and hyperuniform material lacks long-range translational order and exhibits no Bragg scattering, but nevertheless results in isotropic photonic bandgaps. These bandgaps, furthermore, support freeform waveguides that are impossible to fabricate in photonic crystals. The waveguide embodiments of the invention channel photons robustly in arbitrary directions with facile control of transmission bandwidth (which facilitates filtering), and have the ability to guide both polarizations of radiation through the same waveguide channel. Moreover, as noted supra, the waveguides can be decorated to produce sharp resonant structures. The potential of photonic, phononic and electronic devices fashioned in hyperuniform disordered structures is thus demonstrated, opening the way for novel application to technologies including but not limited to displays, lasers (Cao, H. et al., Phys. Rev. Lett. 82: 2278, 1999), sensors (Guo, Y. et al., Optics Express 16: 11741, 2008), telecommunication devices (Noda, S. et al., Nature 407: 608, 2000, and optical micro-circuits (Chutinan, A. et al., Phys. Rev. Lett. 90: 123901, 2003).

By way of example but not of limitation, U.S. Pat. No. 6,990,259 (incorporated herein by reference for all purposes) describes a photonic crystal defect cavity biosensor, and its construction and use. The findings disclosed herein by Applicants show that defect cavities in hyperuniform disordered materials perform as well or better. Accordingly, defect cavity biosensors constructed as taught in U.S. Pat. No. 6,990,259 but employing hyperuniform disordered materials instead of periodic crystalline materials are expected to be used in the same way to good effect. Similarly useful would be the photonic elements described in United States Patent Application 2010/027986 realized in a hyperuniform disordered material.

Applicants have also shown that hyperuniform disordered materials can support electromagnetic sensors that rely on waveguides. Thus, the guidance provided to make and use electromagnetic sensors based on waveguides realized in photonic crystals also serves for constructing and using similar sensors realized in hyperuniform disordered materials. U.S. Pat. No. 7,731,902 (incorporated herein by reference for all purposes) provides such guidance for an interferometric sensor, a sensor that measures changes in the refractive index of a fluid, wherein the changes are referable to the concentration of a target or analyte in the fluid, and a sensor having a photonic element whose refractive index changes as a result of the deposition of a target on the photonic element or as a result of a binding of a target to the photonic element.

Figure 6:
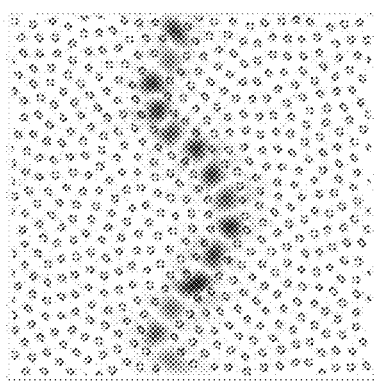
FIG. 6 shows electric field distributions in point defects that form a sinusoidal wave guide in a hyperuniform disordered structure.

The distribution of dielectric material around bend junctions in bandgaps fashioned in the hyperuniform disordered materials is always statistically isotropic. Therefore, if the defect mode created by the removal of material falls within the PBG, the bend can be oriented at any arbitrary angle. The light propagating through the unusually-shaped waveguide channel simulated by removing dielectric cylinders along the sinusoidally-shaped path (FIG. 6) is tightly confined in the transverse direction, penetrating only in the next few rows of dielectric cylinders. Calculations showed that the transmission reached a maximum of about 83%. Backscattering of the propagating mode, although likely in such channels, can be alleviated by optimizing the cylinder size along the channel such that localized resonances similar to those that arise in point-like defects "entrain" along the channel to guide light through the channel.

Figure 14:
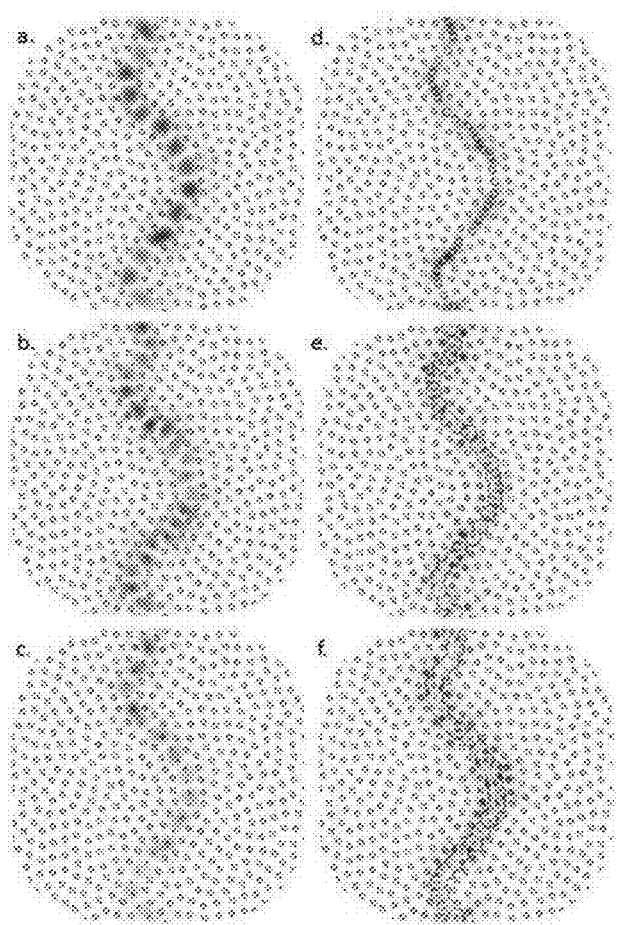
FIG. 14 shows higher order modes in the waveguide channel of FIG. 6.

The hyperuniform disordered structures analyzed here yielded large photonic band gaps of around 40% of the central frequency. FIG. 14 shows higher-order guided modes obtained by varying the radius of the defect cylinders along the channel path.

The ability to construct waveguides oriented in virtually any direction allows the artisan to interconnect waveguides and cavities at junctions such that the interconnected channels can be in photonic communication with one another no matter what the relative orientations of the waveguides. Moreover, each waveguide in the interconnected system can be "outfitted" with its own set of line defects and point defects, so that a system may serve as a means of splitting a band of frequencies into two or more sub-bands having selectable frequencies. Since the transmission of each sub-band is independently tunable in each segment of each waveguide, a photonic signal entering the system can be narrow-band filtered within any system to create a virtually unlimited number of specific systems. Highly advantageous in optical circuit design, for example, the designer has essentially unlimited flexibility to design waveguides that accommodate any band structure and as much flexibility in laying out the waveguide channels for any particular circuit.

Cavity Modes.

Figure 9:
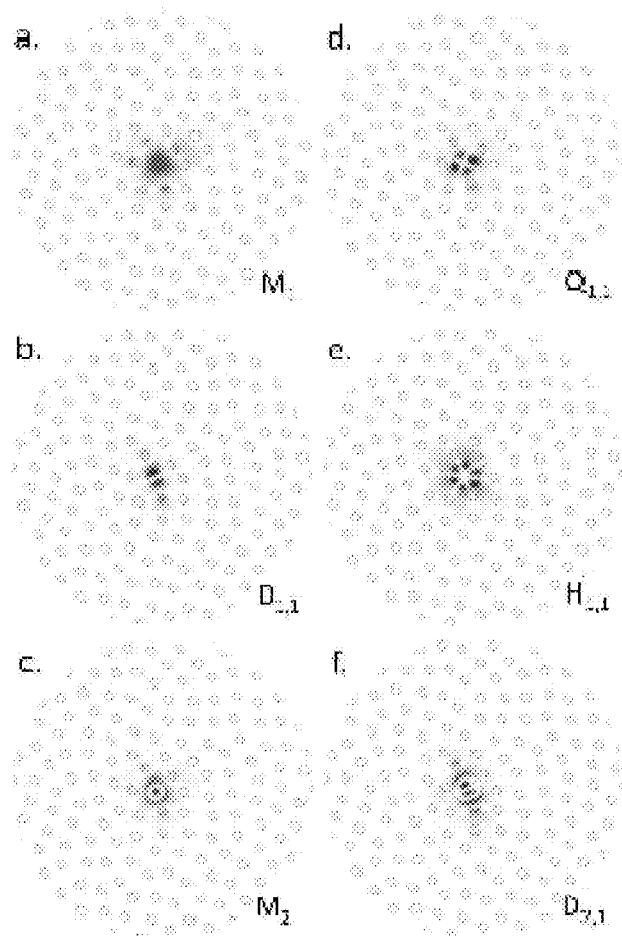
FIG. 9 shows electric field distributions for cavity modes of different symmetries obtained by changing the size of the defect.
Figure 10:
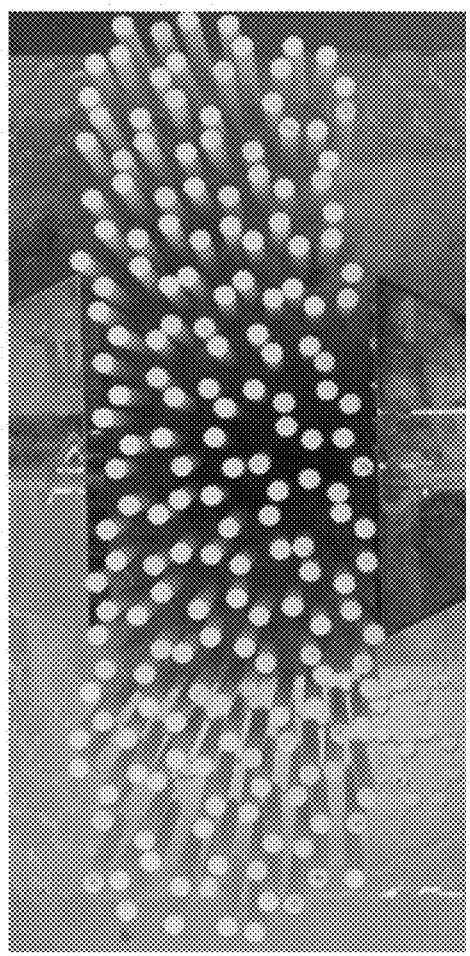
FIG. 10 is a photograph of a hyperuniform disordered structure showing the experimental setup for interrogating a slice of the structure.

According to recent unpublished simulation studies by Florescu et al., introducing a point defect by removing a single dielectric cylinder from a 2D hyperuniform PBG structure results in a localized cavity mode with monopole symmetry. The electric field oscillation pattern was predicted to extend 1-2 cell widths into the surrounding structure (FIG. 9). When a defect dielectric cylinder of increasing radius was used to replace a regular one, the electric field of the localized cavity modes would oscillate with changing symmetries. For every symmetry order, such as monopole, dipole, quadrupole, hexapole and octopole, it was observed that an increase in defect cylinder radius introduced higher resonant frequencies inside the PBG region. Cavities are easily generated and changed in this structure by removing rods to create voids and placing bundled clusters of rods into the voids. Horn antennas attached to a microwave vector network analyzer were used to measure the reflection and transmission through a slice of the hyperuniform disordered structure, a few wavelengths thick, with and without those cavities (FIG. 10).

Figure 15:
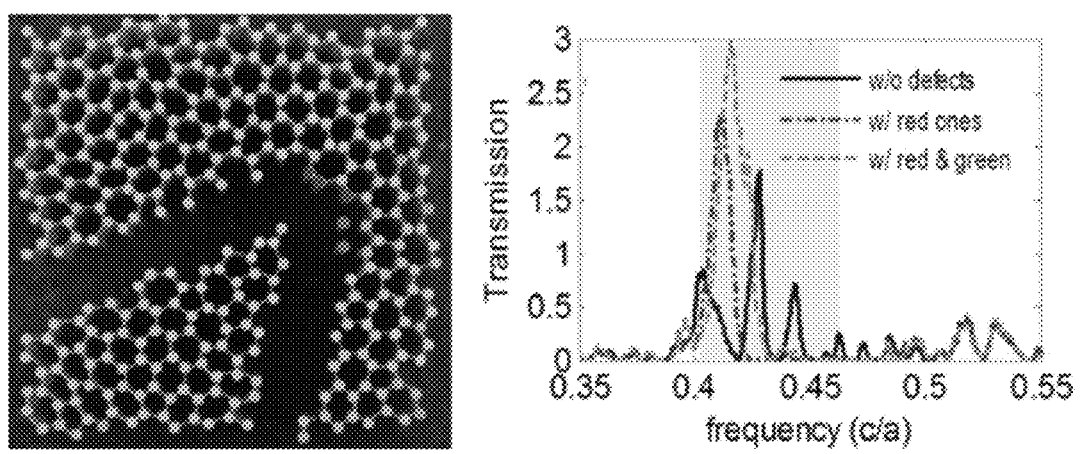
FIG. 15 shows a photo of and transmission profiles through a 50° bend in an experimental waveguide.

The great flexibility in tuning these cavity modes in the hyperuniform disordered structure, combined with its isotropy, makes it possible to guide and filter light of desired frequencies around arbitrarily sharp bends. FIG. 15 shows a photo of and transmission through a 50° bend, which can be considered as two straight channels joined by a cavity at the corner. Waves of various frequencies prohibited from propagating in the bulk PBG material PBG are guided and transmitted in the waveguide channel through this sharp bend. The resonant frequencies in this cavity were modified and optimized by adding and removing various rods. This flexibility and abundance of cavity modes are important for filtering and tuning applications.

Thus, sharp PBG resonant modes are shown by experiment to be attainable in a hyperuniform disordered structure, and the frequency of the modes can be tuned by varying the dielectric defects inside the cavity as predicted by simulations. The ability to control and localize modes of different symmetry and frequency in the same physical cavity and to guide light through modes with different localization properties can have a great impact on all-optical switching and single-atom laser systems (Florescu, M. and John, S., Phys. Rev. A 69: 053810, 2004; Florescu, L. et al., Phys. Rev. A 69: 013816, 2004). The new cavity and waveguide architectures are promising candidates for achieving highly flexible and robust platforms for integrated optical microcircuitry.

EXPERIMENTAL

Example 1 Simulation

The finite-difference time-domain (FDTD) method (Yee, K., IEEE Trans. Antennas Propag. 14: 302 1966) was used to calculate the propagation of light inside the hyperuniform disordered photonic structures. A computational domain with periodic boundary conditions in the transverse direction and perfectly matched layer (PML) condition in the normal direction was employed. The spatial resolution in these numerical experiments was at least n=64 mesh points per a, and the temporal resolution was $0.5/n \times a/c$, where c is the light speed in vacuum. For transmission calculations, a broadband source was placed at one end of the computational domain and the transmission signal was recorded at the other end with a line-detector (Oskooi, A., et al., Comp Phys. Comm 181: 687, 2010). The Fourier components of the field were then evaluated and the spectra averaged and normalized to the transmission profile in the absence of the structure. For quality factor calculations (Irvine, W., Phys. Rev. Lett. 96: 057405, 2006), the modes were excited with a broadband pulse from a current placed directly inside the cavity. After the source was turned off, the fields were analyzed, and frequencies and decay rates of the confined modes evaluated (Oskooi, A., et al., Comp Phys. Comm. 181: 687, 2010). To calculate photonic band structures, a supercell approximation was employed using the conventional plane-wave expansion method (Johnson, S. and Joannopoulos, J., Optics Express 8: 173, 2001; Liang, W. et al., Phys. Rev. E 67: 026612, 2003).

Figure 4:
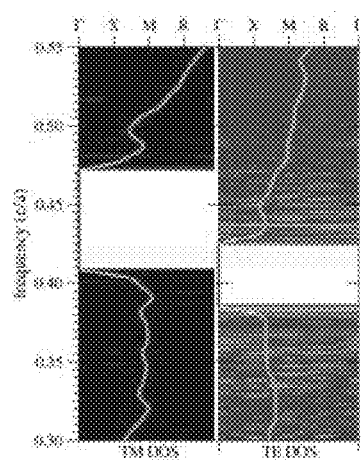
FIG. 4 shows the Finite Difference Time Domain (FDTD) simulations of (left) TM and (right) TE band structures (blue and red curves) and Density of States (DOS) (green curve) for the structure shown in FIG. 1.

FIG. 4 shows FDTD simulations of (left) TM and (right) TE band structure (blue and red curves) and DOS (green curve) for the hyperuniform structure shown in FIG. 1*a*. The complete band gap region is shown by the peach colored area. The PBGs shown are equivalent to the fundamental band gap in periodic systems: the spectral location of the TM gap, for example, is determined by the resonant frequencies of the scattering centers, and always occurs between band N and N+1, with N precisely the number of cylinders per supercell. Similarly, for TE polarized radiation the band gap always occurs between bands N and N+1 where N is now the number of network cells in the structure.

Figures 16A, 16B:
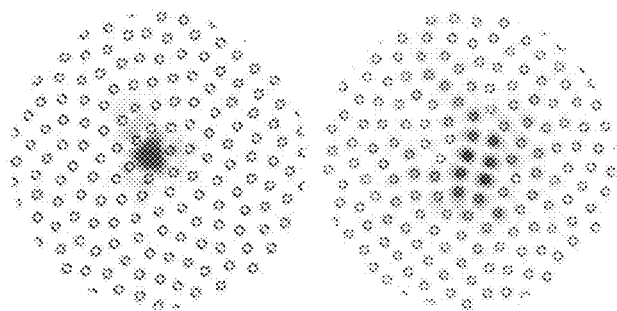
FIG. 16 shows a simulated cavity mode obtained by removing one of the dielectric cylinders (FIG. 16a) contrasted to an unperturbed hyperuniform disordered structure (FIG. 16b).
Figure 17:
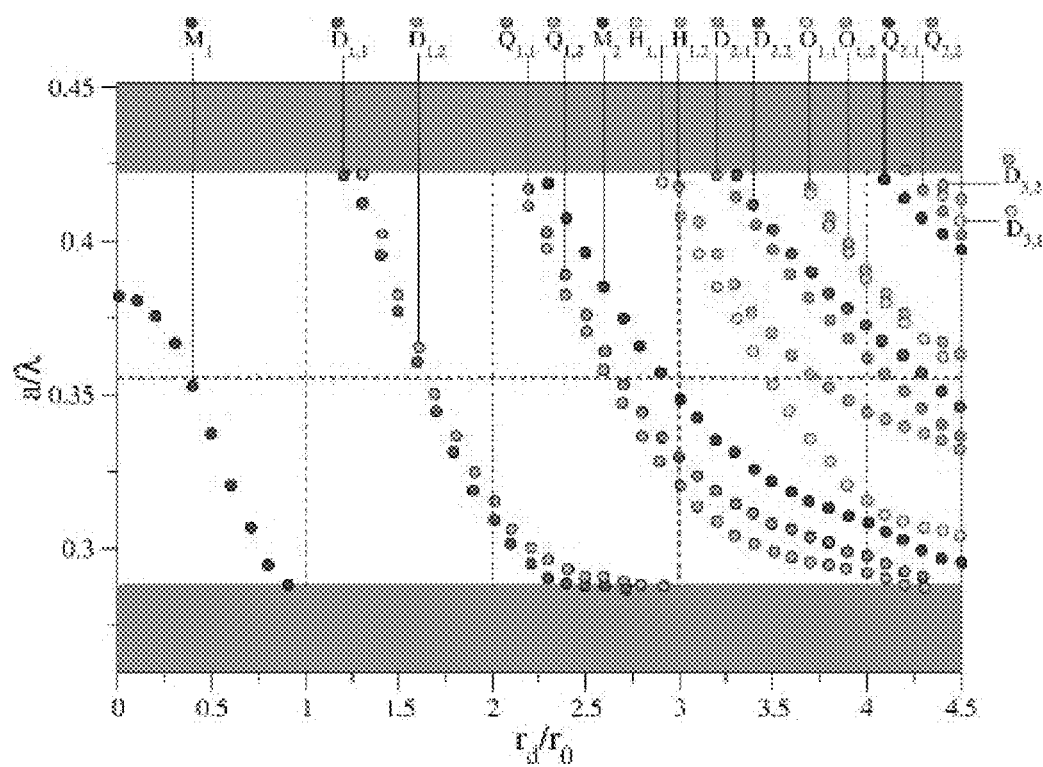
FIG. 17 shows the electric field mode distribution as calculated for a few selected localized modes.

In an otherwise unperturbed hyperuniform disordered structure, it is possible to create a localized state of the electromagnetic field by reducing or enhancing the dielectric constant at a certain point in the sample. In two-dimensional structures, this can be realized by removing one of the cylinders. Due to the presence of the point-like defect, a localized cavity mode is created within the photonic band gap at a certain frequency. FIG. 16 shows a cavity mode obtained by removing one of the dielectric cylinders from a hyperuniform disordered structure. Note that the electric field distribution is highly localized around the defect, extending only up to distances involving 1-2 rows of cylinders beyond the position of the missing cylinder. The quality factor of the two-dimensional confined mode is higher than $10^8$. The nature of the localization mechanism around this type of defect in hyperuniform disordered materials is rather different from the Anderson-like localization mechanism naturally present in this as well as conventional disordered structures. FIG. 16*b* shows a localized photonic mode in the unperturbed hyperuniform disordered structure has a localization length that is 5-6 times larger than that in the cavity mode.

Figure 18:
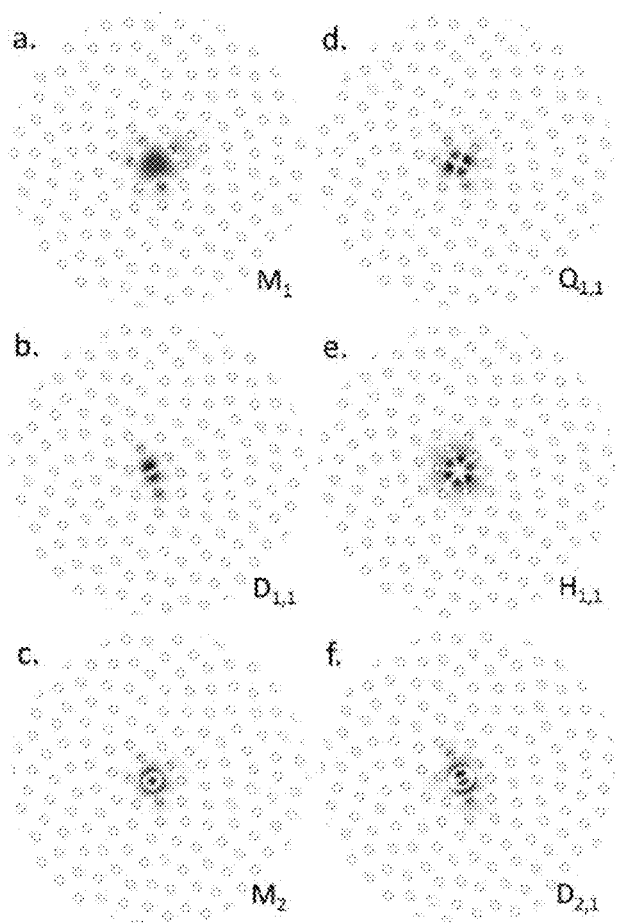
FIG. 18 shows the evolution of the localized modes associated with a defect cylinder as a function of the dimensionless defect radius.

In this system, the evolution of localized modes associated with a cylinder perturbed by varying its radius can be tracked. When the radius is reduced, a single mode from the continuum of modes below the lower photonic band edge is pulled inside the PBG and becomes localized. If the radius of the cylinder is increased, a number of modes (the precise number is determined by the relative size of the defect cylinder) from the continuum of modes above the upper photonic band edge are pulled inside the PBG. FIG. 18 shows the electric field mode distribution for a few selected localized modes. Note the nearly perfect monopole (M), dipolar (D), quadrupolar Q), and hexapolar (H) symmetries associated with certain modes. Different localized modes are indexed based on their approximate symmetry (M, D, H, . . . ), where the first index refers to the order of the mode and the second index refers to the number of modes of a given order (e.g., D1,2 is the second mode of first-order with a dipole-like symmetry).

In FIG. 20 the evolution of the localized modes associated with a defect cylinder as a function of the dimensionless defect radius is tracked. The dimensionless defect radius in this example is $r_D/r_0$. For a defect radius $r_D/r_0=0.47$ (where $r_0$ is the radius of the unperturbed cylinders), the defect mode reaches the mid-point of the PBG and is maximally protected from interactions with the propagating modes from the continua below and above the photonic band gap. When the radius of the defect cylinder is increased, it becomes possible to accommodate more localized modes in the defect region, distinguished either by their approximate symmetry or frequency. For $r_D/r_0=4$, a total of 12 localized modes can coexist within the same defect. However, it should be noted that at these large radii, the defect cylinders start to overlap with the surrounding cylinders and the confinement decreases.

In photonic crystals, removing a row of rods generates a channel through which light with frequencies within the band gap can propagate, a so-called crystal waveguide. Light cannot propagate elsewhere in the structure outside the channel because there are no allowed states. The waveguides must be composed of segments whose orientation is confined to the high-symmetry directions of the crystal. As a result, the waveguide bends of 60° or 90° can be easily achieved, but bends at an arbitrary angle lead to significant radiation loss due to excessively strong scattering at the bend junction and require additional engineering to function properly.

Example 2: Construction of Disordered 2D Arrangements of Dielectric Materials with Bandgaps Comparable to Those in Photonic Crystals for the Same Dielectric Constant The key features of the design are: (1) a disordered network of dielectric cylinders and walls in which each cylinder is connected to three neighbors (trivalency); and (2) the cylinder centers are generated by a point pattern in which the number variance of points in a "window" of radius, R, $\sigma(R)=(N_R^2)-(N_R)^2$ is proportional to R (hyperuniformity). Note that, for a 2D random Poisson distribution, $\sigma(R) \propto R^2$ is proportional to the area, whereas crystals and quasicrystals have $\sigma(R) \propto R$. Because of these two features, the photonic design pattern has uniform nearest neighbor connectivity and hyperuniform long-range density fluctuations or, equivalently, a structure factor with the property $S(k) \to 0$ for wavenumber $k \to 0$ (Torquato, S. and Stillinger, F., Phy. Rev. E 68: 041113-1, 2003) similar to crystals; at the same time, the pattern exhibits random positional order, isotropy, and a circularly symmetric diffuse structure factor S(k) similar to a glass. While it is not necessary to propose any mechanism for how embodiments of an invention work, and no such limitation is intended, it is believed that the novel combination of the foregoing characteristics enables Mie resonances in individual cylinders to couple in "bonding" and "antibonding" modes that concentrate electrical field either in cylinders or in air cells separated by a band gap, reminiscent of the band edge states in the periodic crystals and in Si. Although this Example focuses on 2D architectures, it is to be understood that the same design principles can be applied to 3D architectures using techniques well-known to persons skilled in the art.

Example 3. "Stealthy" Systems

A subclass of 2D hyperuniform patterns comprise designs having the largest band gaps for a given dielectric contrast (Florescu et al., PNAS 106: 20658, 2009). These "stealthy" designs, as noted supra, have a structure factor S(k) precisely equal to zero for a finite range of wavenumbers $k<k_C$ for some positive $k_C$. Stealthiness means that intermediate as well as long-range density fluctuations are similar to crystals. At the same time, when combined with the condition that the structure be derived from a point pattern, increasing $k_C$ results in a narrowing of the distribution of nearest-neighbor distances. The net effect is to increase the band gap. This Example is the first physical realization of a hyperuniform stealthy design (FIG. 1) using commercially purchased $Al_2O_3$ cylinders and walls cut to designed heights and widths. The dielectric constant of these $Al_2O_3$ materials was measured to be 8.76 at the mid-gap frequency. The hyperuniform pattern consists of cylinders with radius r=2.5 mm connected by walls with thickness t=0.38 mm and various widths to match the hyperuniform network: the components are 10 cm in the third dimension. The average inter-cylinder spacing is a=13.3 mm and the sample size used in the transmission measurements was 13a×13a, the region inside the red square in FIG. 1(a). A platform in the desired hyperuniform pattern with slots of depth 1 cm for the insertion of cylinders and walls was fabricated by stereolithography. A side view of the structure, FIG. 1(b), shows the patterned platform and the inserted cylinders and walls. Cylinders and walls can easily be removed and replaced to make cavities, waveguides, and resonance structures. FIG. 1(c) is a top view.

Samples for investigative use herein were fabricated by decorating hyperuniform point patterns with cylindrical rods with dielectric constant f=11.56 and radius r/a=0.189. These values were chosen to optimize the size of the photonic band gap. The hyperuniform point patterns were generated using the collective coordinate method set forth in Torquato, S. and Stillinger, F., Phys. Rev. E 68: 04113, 2003 with stealthy order parameter $\chi$=0.5. (Also appears in Description)

Experimentally, microwaves in the spectral range of 7-13 GHz, $\lambda \sim 2a$ were used, and a setup similar to the one described in Man, W., et al. Nature, 436: 993, 2005. The sample was placed between two facing microwave horn antennas. For band gap measurements, the horns were set a distance of 28a apart to approximate plane waves. Absorbing materials were used around the samples to reduce noise. The transmission is defined as the ratio between transmitted intensity with and without the sample in place. For the hyperuniform disordered structure shown in FIG. 1b, measured transmission normal to the sample boundary was plotted in FIG. 2a (TE) and FIG. 2c (TM). The regions of low transmission agree well with the calculated TE band gap (blue stripe in FIG. 2a) and TM band gap (blue stripe in FIG. 2c). The complete PBG region is where the two stripes overlap.

Example 4 Angular Dependence of the Photonic Properties

Figure 2:
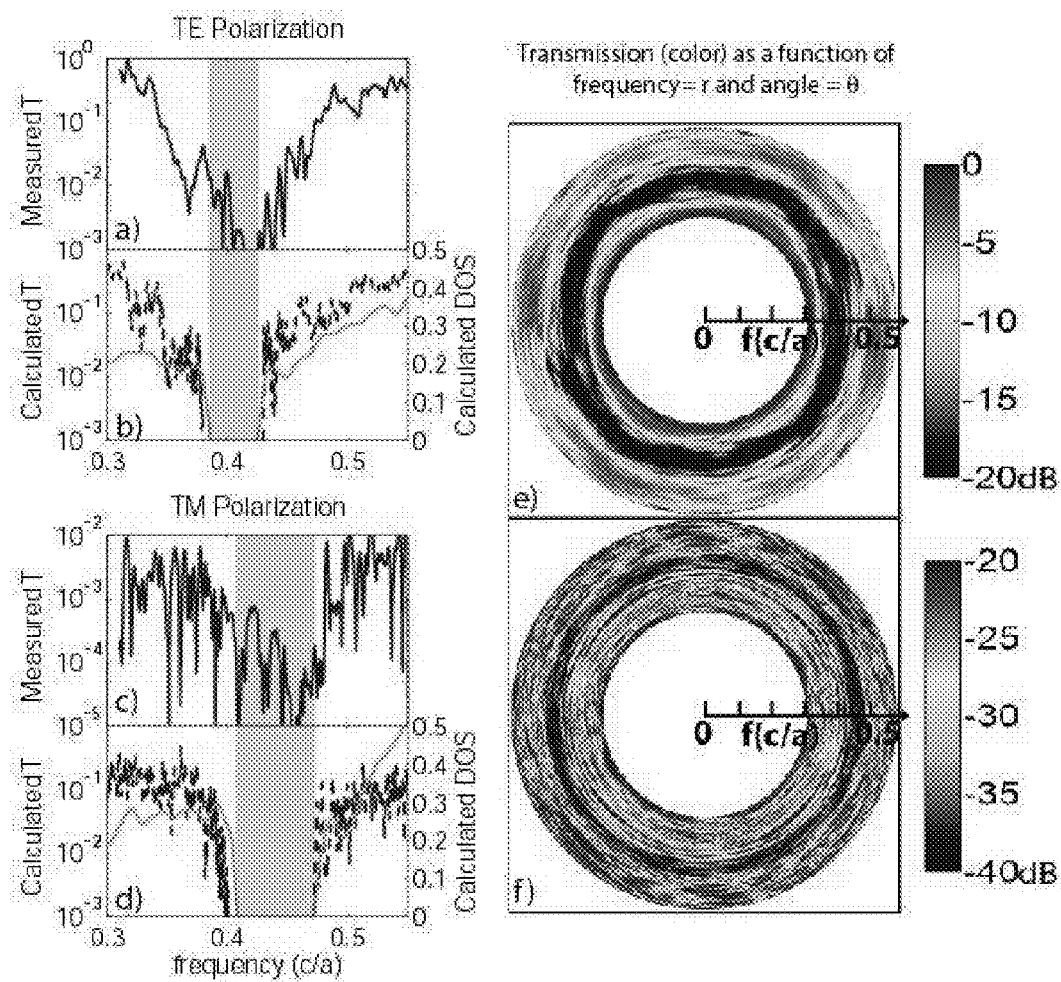
FIG. 2 shows the measured transmission spectrum and calculated transmission and density of state (DOS) for the hyperuniform sample.
Figure 5:
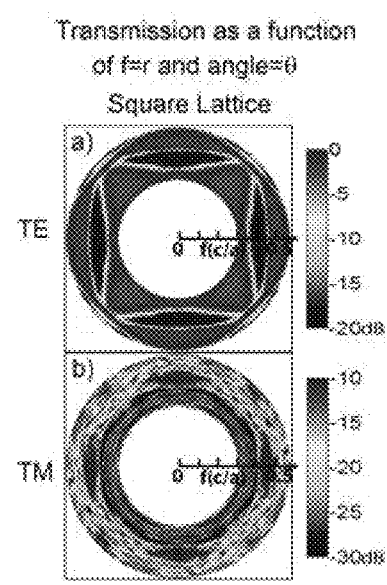
FIG. 5 shows the measured transmission as a function of frequencies (f=r) and incident angles (θ=θ) for square lattice of (r=2.5 mm, t=0.38 mm, a=13.3 mm).

Cylinders and walls were removed from the corners of the samples to construct a circular boundary of diameter 13a. The samples were rotated along the axis perpendicular to the patterned plane, and the transmission was recorded every two degrees for both TE and TM polarizations. In FIGS. 2e and f, 3D color plots of T(r=f, $\theta$=$\theta$) were used in the cylindrical coordinate system (Man, W. et al. Nature 436: 993, 2005) to present the measured transmission T as a function of frequency, f, and incident angle, $\theta$. The results for the hyperuniform structure show an isotropic complete PBG (circular blue ring) with relative T<−20 dB at f=0.42 c/a, (c=light speed) for both polarizations. A similar square lattice was constructed and measured for comparison, shown in FIG. 5. Measured transmission as a function of frequencies (f=r) and incident angles ($\theta$=$\theta$) for the square lattice of (r=2.5 mm, t=0.38 mm, a=13.3 mm). In a) stop gaps due to Bragg scattering occur at the Brillouin zone boundaries, change frequency in different directions, and do not overlap to form bandgap for TE polarization. In b) stop gaps show angular dependence associated with 4-fold rotational symmetry, and are able to overlap in all directions for TM polarization. Through the square lattice, the measured TM polarization transmission is also significantly lower than the TE polarization transmission.

The measured transmitted power was much lower for TM polarization than for TE polarization in both the hyperuniform sample and the square lattice sample. For each polarization, the transmitted power was limited by the horn geometry, namely the rectangular shape and the relatively small radiation acceptance angle of 15°.

The experimental results are compared with the theoretical predictions obtained using a super-cell approximation and the conventional plane-wave expansion method (Joannopoulos, J. et al. Photonic Crystals: Molding the Flow of Light ($2^{nd}$ Ed.) Princeton University Press, 2008; Johnson S. and Joannopoulos, J., Optics Express 8: 173, 2001) to numerically calculate the band structure of the system. The size of the super-cell applied for the simulation is 22a×22a as shown in entire region of FIG. 1a. Finite difference time-domain (FDTD) simulations of the transmission spectrum through a finite sample of 22a×22a (blue curves in FIGS. 2b and d) show regions of considerably reduced transmission in the spectral region of the PBGs and overlap the experimental results. Due to background dark noise (around −40 dB), the experiment was limited to detecting a gap contrast of less than −30 dB, though the simulations of the finite sample indicated suppression by six orders of magnitude. The calculated density of states (DOS) (green curves in FIGS. 2b and d) for both TE and TM modes was zero within the PBG. Band structures for the TE and TM mode of the system are shown in FIG. 4.

Example 5 Waveguides

In order to test whether light can be guided through the hyperuniform disordered structure, channels were created by removing two rows of cylinders and walls along a line, as shown in FIG. 3a. The horn antennas were placed right next to the end of the channel for the transmission measurement. For a completely open channel, without any defect cylinders inside, the TM transmission spectrum is shown in FIG. 3b, while the calculated TM polarization gap is highlighted with shading. Transmission through the channels is defined relative to transmission intensity between two facing horns separated by the channel length. A broad band of frequencies were guided through the open channel with very high transmission. When a few roughly evenly spaced defect cylinders were placed inside the open channel, a sharp resonant transmission peak appeared. Importantly, the resonant frequency in these coupled resonant waveguides can be easily tuned by modifying the position of the defect cylinders. Two sets of defect cylinders marked as red or green dots in FIG. 3a were added separately. Their corresponding transmission spectra are shown in FIG. 3c with red dash dot line or green dash line, respectively. The coupled resonator waveguide can be finely tuned acting as a narrow band pass filter with a high Q factor.

In photonic crystals, waveguides are limited in their direction and angularity by crystal symmetries (Lin, S-Y et al. Science 282: 274, 1998). Without suggesting any limitation based on theories of why embodiments of the invention work, it seems likely that the disorder and isotropy in the hyperuniform patterns relax many of the restrictions found in periodic structures. The flexibility of the experimental sample employed in these Examples makes it easy to form channels with arbitrary bending angles and to decorate their sides, corners and centers with cylinders and walls for tuning and optimizing the transmission bands. FIG. 3d shows a waveguide with a sharp 50° bend made by removing cylinders and walls in a path ~2a wide. FIG. 3e shows the measured transmission. The transmission is comparable to that in the straight channel with unity transmission despite the sharp bend, and it is adjustable by modifying defects. Even more remarkable is the "S" shaped freeform waveguide shown in FIG. 3f. As in the previous channels, the transmitting and receiving horns are parallel to the input and output of the channel and the transmission is of order unity (FIG. 3g). Again, transmission bands can be easily improved and flexibly tuned using defect cylinders.

The foregoing Examples have experimentally demonstrated for the first time three significant results. First, an isotropic complete PBG was obtained, Δf/f=4.0%, (all angles and all polarizations) in a 2D disordered hyperuniform dielectric material at dielectric contrast of 8.76. Unlike photonic crystals, the sample material is disordered and hyperuniform, lacking long-range translational order and Bragg scattering, yet results in isotropic photonic bandgaps. Furthermore, the isotropic PBG permitted fabrication of freeform waveguides impossible for photonic crystals. The freeform guides can channel photons robustly in arbitrary directions with facile control of transmission bandwidth and sharp filtering. Finally, the waveguides can be decorated to produce sharp resonant structures. These phenomena illustrate the potential of hyperuniform disordered structures for producing photonic, phononic and electronic materials with novel physical properties and technological applications.

Example 6: Frequency Splitters and Narrow-Band Filters

Figure 7:
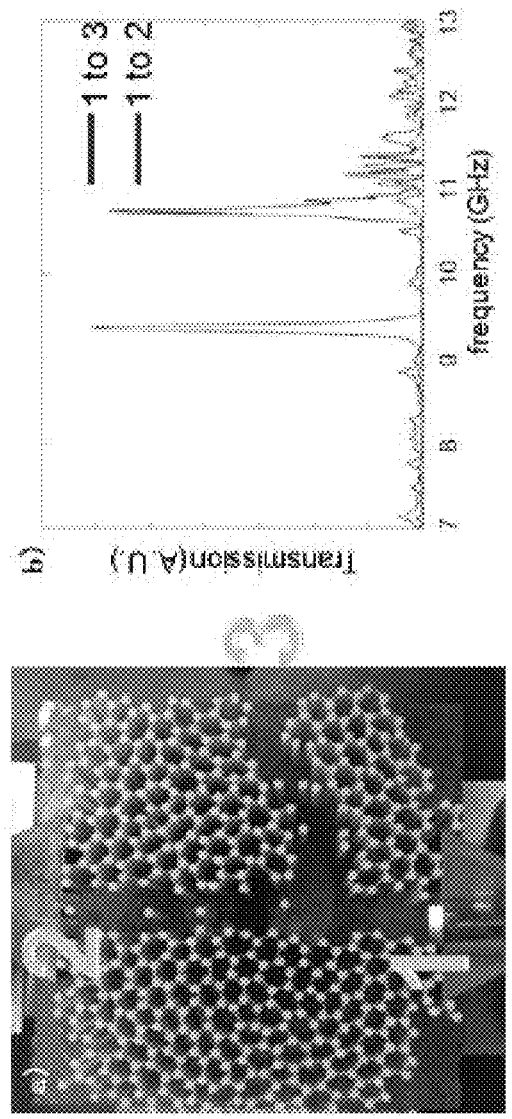
FIG. 7 shows a photograph of a "Y" junction for frequency splitting and plots of transmission vs. frequency for each branch.

FIG. 7 shows a "Y" shape junction for frequency splitting. Continuous waves of different frequencies were sent into the input port marked as "1" on the photo. Transmissions were measured separately at two different output ports marked as "2" and "3", respectively. At the same time, signals of different frequencies were directed into different branches automatically. The disordered hyperuniform PBG material offers a very flexible platform for defect design to select tunable frequencies, therefore the transmission peaks through two branches of the "Y" shape junction can be controlled and tuned by arranging different distribution of extra defect cylinders in the two output branches.

Figure 8:
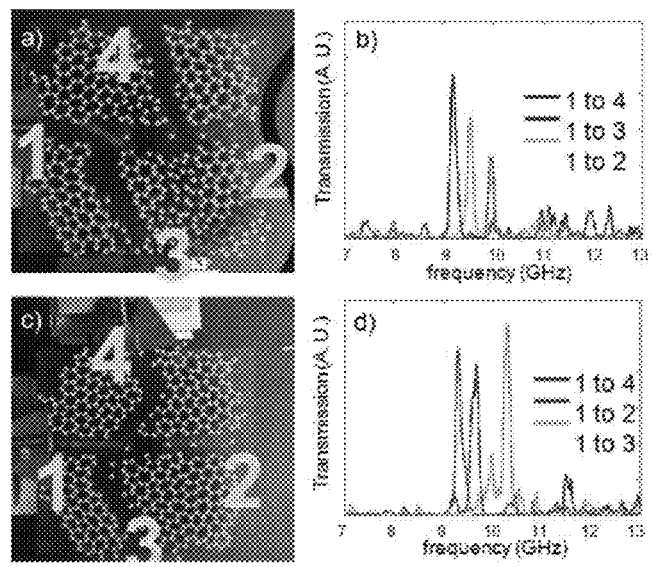
FIG. 8 shows 2-step and 3-way frequency splitters and plots of transmission vs. frequency for each guide path.

FIG. 8 a) and b) show a two-step frequency splitter, c) and d) a three-way frequency splitter. Again, signals of different frequencies are automatically directed into different branches in various architectures. The propagating modes are strongly related to resonances built up inside the channel, enabling us to design local defects to control the passing frequency of each channel.

Experimentally, stereolithography was used to fabricate the bases of the structures at the scale of average spacing a=13.3 mm. Commercially available 100.0 mm tall $Al_2O_3$ cylinders of radius r=2.5 mm and thin sheets of thickness t=0.38 mm of various width were used to assemble the hyperuniform network structure. The photonic properties were measured using a HP-8510C vector network analyzer for microwaves with wavelength comparable to twice the cylinder spacing. The structure has a TM polarization PBG from 9.2 to 10.7 GHz and a TE polarization PBG from 8.7 to 9.6 GHz. Wave-guiding channels were constructed and modified by removing rows of building blocks and adding individual extra defect cylinders. Transmission through the channels was measured by placing two microwave horn antennas right next to the channel openings. Absorption materials were placed around the sample to reduce noise.

The experiments have demonstrated novel architectures for freeform waveguides of arbitrary shapes, as well as compact frequency splitters with flexible tuning abilities, in isotropic PBG material. The ability to guide and split EM waves in a freeway format make this new class of disordered PBG materials good candidates for achieving highly flexible and robust platforms for integrated optical and other electromagnetic circuits.

Example 7: Cavity Architectures

The experimental structure (FIG. 9) for this example was assembled using $Al_2O_3$ cylindrical rods (r=2.5 mm, h=10 cm), inserted into a platform of a hyperuniform disordered pattern with 1 cm deep slots. The average cell size (spacing between rods) was a=13.3 mm. The structure had TM polarization PBG of 9.2 to 10.7 GHz. Cavities were easily generated and changed in this structure by removing rods to create voids and placing bundled clusters of rods into the voids. Horn antennas attached to a microwave vector network analyzer were used to measure the reflection and transmission through a slice of the hyperuniform disordered structure, a few wavelengths thick, with and without those cavities (FIG. 10).

Figure 11:
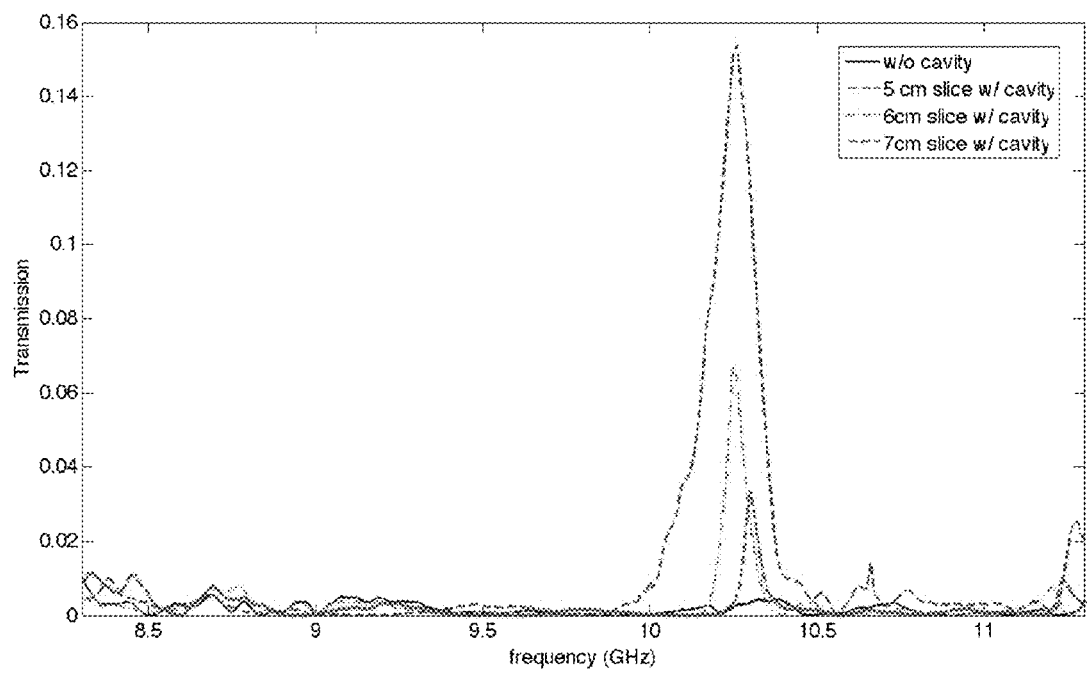
FIG. 11 is a plot of TM polarization transmission through slices of varying thickness.

As shown in FIG. 11, cavity modes were revealed by large transmission peaks inside the PBG frequency region. By removing two cylinders in the middle of the structure, cavity modes around 10.3 GHz were excited. The transmission peaks associated with those cavity modes decreased exponentially with the thickness of the sample slice, and still remained detectable when the cavities were at a distance of 2.5a away from the sample edge.

Figure 12:
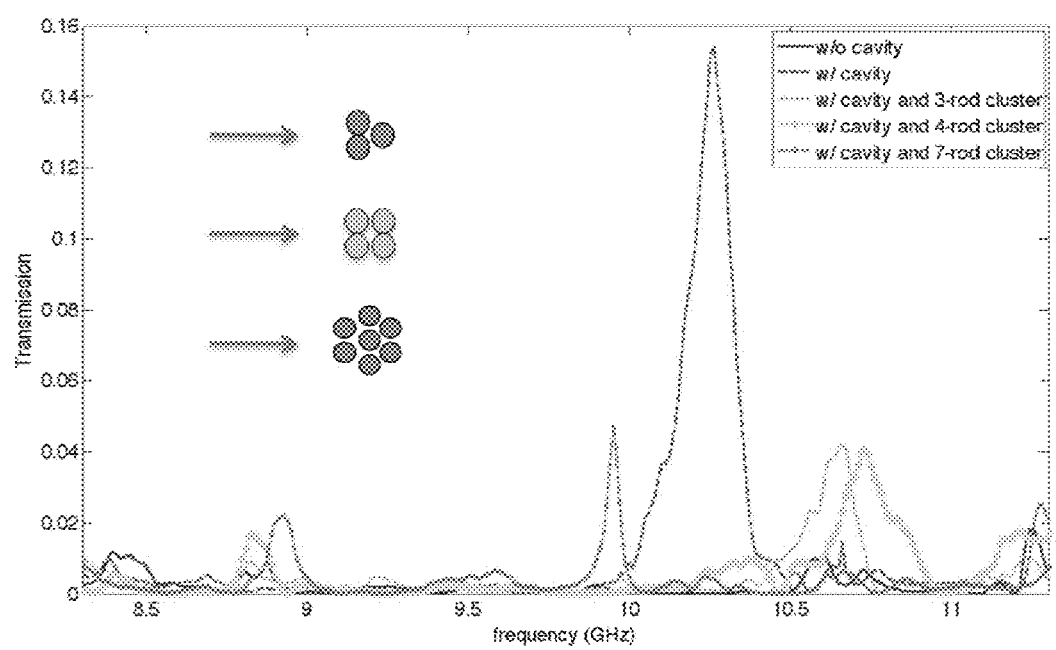
FIG. 12 is a plot of TM polarization transmission for various rod configurations.

To investigate the symmetry properties of the cavity modes, bundled clusters of alumina rods were introduced in different arrangements and orientations. As was predicted in the simulation study, an increase of the high-index dielectric defect radius pushed the resonant frequency higher for a particular order of symmetry mode. As shown in FIG. 12, introducing a 3-rod, 4-rod, and 7-rod cluster, respectively, resulted in various resonant peaks of different cavity modes.

Figure 13:
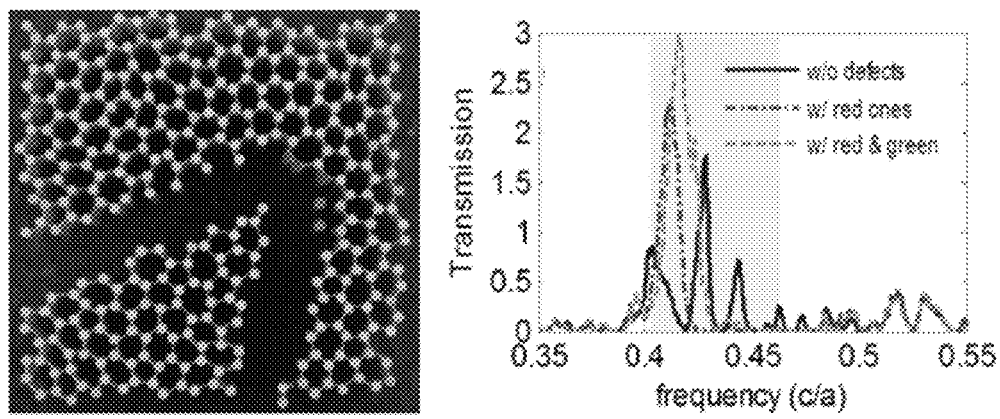
FIG. 13 is a photograph of a filtering waveguide showing particular cavity mode modifications and a plot of TM polarization transmissions for each modification.

The great flexibility in tuning these cavity modes in the hyperuniform disordered structure, combined with its isotropy, makes it possible to guide and filter light of desired frequencies around arbitrary sharp bends. FIG. 13 shows a photo of and transmission through a 50° bend, which can be considered as two straight channels joined by a cavity at the corner. Waves of various frequencies inside the PBG were guided and transmitted through this sharp bend. The resonant frequencies in the cavity were modified and optimized by adding and removing various rods. This flexibility and abundance of cavity modes are important for filtering and tuning applications.

The results demonstrate that sharp PBG resonant modes are attainable in a hyperuniform disordered structure, and the frequency of the modes can be tuned by varying the dielectric defects inside the cavity as predicted by simulations. The ability to control, localize, and slow down EM waves inside solids will have a great impact on future technological development of optical and other electromagnetic switches, lasers and sensors.

The references cited throughout this application are incorporated for all purposes apparent herein and in the references themselves as if each reference was fully set forth. For the sake of presentation, specific ones of these references are cited at particular locations herein. A citation of a reference at a particular location indicates a manner in which the teachings of the reference are incorporated. However, a citation of a reference at a particular location does not limit the manner in which all of the teachings of the cited references are incorporate for all purposes.

Additional embodiments include any single embodiment herein supplemented with one of more element from any one or more other embodiment herein.

It is understood, therefore, that this invention is not limited to the particular embodiments disclosed, but is intended to cover all modifications which are within the spirit and scope of the invention as defined by the appended claims and the above description.

The invention claimed is:
1. An electromagnetic waveguide fabricated in a hyperuniform disordered photonic material having a complete photonic bandgap for both TM and TE polarized electromagnetic radiation.
2. The electromagnetic waveguide of claim 1, in photonic communication with a second electromagnetic waveguide.

* * * * *